United States Patent
Demartini et al.

(10) Patent No.: US 12,351,851 B2
(45) Date of Patent: Jul. 8, 2025

(54) DISRUPTION OF CDC42 EFFECTORS IN YEAST FOR INCREASED ALCOHOL AND LYSINE PRODUCTION

(71) Applicant: DANISCO US INC, Palo Alto, CA (US)

(72) Inventors: Jaclyn Diana Demartini, Palo Alto, CA (US); Celia Emily Gaby Payen, Wilmington, DE (US)

(73) Assignee: DANISCO US INC., Palo Alto, CA (US)

(*) Notice: Subject to any disclaimer, the term of this patent is extended or adjusted under 35 U.S.C. 154(b) by 704 days.

(21) Appl. No.: 17/621,957

(22) PCT Filed: Jun. 22, 2020

(86) PCT No.: PCT/US2020/038910
§ 371 (c)(1),
(2) Date: Dec. 22, 2021

(87) PCT Pub. No.: WO2020/263732
PCT Pub. Date: Dec. 30, 2020

(65) Prior Publication Data
US 2022/0251608 A1    Aug. 11, 2022

Related U.S. Application Data

(60) Provisional application No. 62/865,448, filed on Jun. 24, 2019.

(51) Int. Cl.
| | |
|---|---|
| *C12P 7/06* | (2006.01) |
| *C10L 1/02* | (2006.01) |
| *C12N 1/18* | (2006.01) |
| *C12N 15/52* | (2006.01) |
| *C12N 15/81* | (2006.01) |
| *C12P 13/08* | (2006.01) |

(52) U.S. Cl.
CPC .................. *C12P 7/06* (2013.01); *C10L 1/02* (2013.01); *C12N 1/18* (2013.01); *C12N 15/52* (2013.01); *C12N 15/81* (2013.01); *C12P 13/08* (2013.01); *C12Y 102/0101* (2013.01); *C12Y 203/01008* (2013.01); *C12Y 401/02009* (2013.01); *C10L 2200/0469* (2013.01); *C10L 2290/26* (2013.01); *C12N 2800/102* (2013.01)

(58) Field of Classification Search
CPC .... C12P 7/06; C12P 13/08; C10L 1/02; C10L 2200/0469; C10L 2290/26; C12N 1/18; C12N 15/52; C12N 15/81; C12Y 2800/102; C12Y 102/0101; C12Y 203/01008; C12Y 401/02009; Y02E 50/10; C07K 14/395
See application file for complete search history.

(56) References Cited

U.S. PATENT DOCUMENTS

| 8,795,998 B2 | 8/2014 | Pronk et al. |
| 8,956,851 B2 | 2/2015 | Argyros et al. |
| 9,175,270 B2 | 11/2015 | Nevoigt et al. |

FOREIGN PATENT DOCUMENTS

| WO | 2015/023989 A1 | 2/2015 |
| WO | 2015/148272 A1 | 10/2015 |
| WO | 2018/089333 A1 | 5/2018 |
| WO | 2018/226573 A1 | 12/2018 |
| WO | 2019/083879 A1 | 5/2019 |

OTHER PUBLICATIONS

Daniels et al., A role for Gic1 and Gic2 in Cdc42 polarization at elevated temperature, 2018, PLoS ONE 13(12):e0200863. (Year: 2018).*
Daniels et al., A role for Gic1 and Gic2 in Cdc42 polarization at elevated temperature. (2018) PLOS ONE 13(12): e0200863, p. 1-16. (Year: 2018).*
Wang et al., Increasing ethanol titer and yield in a gpd1D gpd2D strain by simultaneous overexpression of GLT1 and STL1 in Saccharomyces cerevisiae, Biotechnol Lett (2013) 35:1859-1864. (Year: 2013).*
International Search Report and Written Opinion from PCT Application No. PCT/US2020/038910 dated Oct. 15, 2020, 9 pages.
Altschul et al., "Basic Local Alignment Search Tool", J. Mol. Bio., 215, Nov. 1990, pp. 403-410.
Altschul et al., "Local alignment statistics", Methods in Enzymology, vol. 266, 1996, pp. 460-480.
Cooper et al., "High-throughput profiling of amino acids in strains of the *Saccaromyces cerevisiae* deletion collection", Genome Research, Cold Spring Harbor Laboratory Press, 2010, pp. 1288-1296.
Devereux et al., "A comprehensive set of sequence analysis programs for the VAX", Nucleic Acids Research, vol. 12, No. 1, 1984, pp. 387-395.
Diepeveen et al., "Evolutionary dynamics in the fungal polarization network, a mechanistic perspective", Biophys Rev vol. 9, No. 4, Aug. 2017, pp. 375-387.

(Continued)

*Primary Examiner* — Robert B Mondesi
*Assistant Examiner* — Naghmeh Nina Moazzami

(57) ABSTRACT

Described are compositions and methods relating to yeast having a genetic mutation that results in decreased amounts of Cdc42 effector proteins, resulting in increased alcohol and lysine production. Such yeast is well-suited for use commercial alcohol production to increase yields and to increase the value of Such yeast is well-suited for use commercial alcohol production to increase yields and to increase the value of amino-acid-containing, fermentation-co-products.

13 Claims, No Drawings
Specification includes a Sequence Listing.

(56) References Cited

OTHER PUBLICATIONS

Duskova et al., "Two glycerol uptake systems contribute to the high osmotolerance of Zygosaccharomyces rouxii", Molecular Microbiology vol. 97, No. 3, 2015, pp. 541-559.
Feng et al., "Progressive sequence alignment as a prerequisite to correct phylogenetic trees", Journal of Molecular Evolution, J Mol Evol, 25, 1987, pp. 351-360.
Ferreira et al. "A Member of the Sugar Transporter Family, Stl1p Is the Glycerol/H+ Symporter in *Saccharaomyces cerevisiae*", Molecular Biology of the Cell, vol. 16, Apr. 2005, pp. 2068-2076.
Henikoff et al., "Amino acid substitution matrices from protein blocks", Proc. Natl. Acad. Sci. USA, vol. 89, Nov. 1992, p. 10915-10919.
Higgins et al., "Fast and sensitive multiple sequence alignments on a microcomputer", Bioinformatics, vol. 5, Issue 2, Apr. 1989, pp. 151-153.
Karlin et al., "Applications and statistics for multiple high-scoring segments in molecular sequences", Proc. Natl. Acad. Sci. USA, vol. 90, Jun. 1993, pp. 5873-5877.
Mulleder et al., "Functional Metabolomics Describes the Yeast Biosynthetic Regulome", Cell, 167, 2016, pp. 553-565.
Needleman et al., "A General Method Applicable to the Search for Similarities in the Amino Acid Sequence of Two Proteins", J. Mol. Biol., 48, 1970, pp. 443-453.
Pearson et al., "Improved tools for biological sequence comparison", Proc. Natl. Acad. Sci. USA, vol. 85, Apr. 1988, pp. 2444-2448.
Qiao, "Routine techniques for monitoring the nutritional value of animal meals", Dissertation, 2001, 224 pages.
Smith et al., "Comparison of Biosequences", Advances in Applied Mathmatics 2, 1981, pp. 482-489.
Thompson et al. "Clustal W improving the sensitivity of progressive multiple sequence alignment through sequence weighting, position-specific gap penalties and weight matrix choice", Nucleic Acids Research, vol. 22, No. 22, 1994, pp. 4673-4680.
Villas-Boas et al., "High-throughput metabolic state analysis: the missing link in integrated functional genomics of yeast", Biochem. J. 388, 2005, pp. 669-677.
Brown et al., "Novel Cdc42-binding proteins Gic1 and Gic2 control cell polarity in yeast", Genes & Development, vol. 11, 1997, pp. 2972-2982.
Chen et al., "The Cdc42 GTPase-associated proteins Gic1 and Gic2 are required for polarized cell growth in Saccharomyces cerevisiae", Genes & Development, vol. 11, 1997, pp. 2958-2971.

\* cited by examiner

DISRUPTION OF CDC42 EFFECTORS IN YEAST FOR INCREASED ALCOHOL AND LYSINE PRODUCTION

CROSS-REFERENCE TO RELATED APPLICATION

This application is a U.S. national stage application under 35 U.S.C. § 371 of International Application No. PCT/US2020/038910, filed on Jun. 22, 2020, entitled "DISRUPTION OF CDC42 EFFECTORS IN YEAST FOR INCREASED ALCOHOL AND LYSINE PRODUCTION," which claims priority to U.S. Provisional Patent Application No. 62/865,448 filed Jun. 24, 2019, the disclosure of which is incorporated by reference herein in its entirety.

INCORPORATION BY REFERENCE OF THE SEQUENCE LISTING

The present application is being filed with a Sequence Listing in electronic format. The Sequence Listing is provided as a file entitled NB41672USPCT_SeqList.txt, created on Nov. 18, 2021, which is 9,799 bytes in size. The information in the electronic format of the Sequence Listing is incorporated by reference in its entirety.

TECHNICAL FIELD

The present strains and methods relate to yeast having a genetic mutation that results in decreased amounts of Cdc42 effector proteins, resulting in increased alcohol and lysine production. Such yeast is well-suited for use in commercial alcohol production to increase yields and to increase the value of amino-acid-containing, fermentation products and co-products.

BACKGROUND

Many countries make fuel alcohol from fermentable substrates, such as corn starch, sugar cane, cassava, and molasses. According to the Renewable Fuel Association (Washington DC, United States), 2015 fuel ethanol production was close to 15 billion gallons in the United States, alone.

In addition to producing about 2.8 gallons of ethanol, a 56-pound bushel of corn processed in a dry mill ethanol plant also generates about 17.5 pounds of animal feed. Animal feed is usually in the form of distillers dried grains with solute (DDGS) and represents the starch-depleted portion of corn plus the biomass of the yeast used for fermentation. Per weight, DDGS is more nutritional for animals than the unprocessed corn because it is more rich in protein and fat. Beyond DDGS, dry mill ethanol plants also have the ability to create other protein-rich corn co-products for animal feed applications.

Lysine is an essential amino acid for most animals and must be supplemented if it cannot be supplied in adequate amounts in DDGS to meet feed conversion expectations. Synthetic lysine is expensive and can represent a significant cost of animal feed. The need exists for ways to improve or maintain the production of alcohol from starch-containing feedstocks while increasing the nutritional value of animal feed co-products.

SUMMARY

Described are compositions and methods relating to yeast cells having a genetic mutation that results in decreased amounts of Cdc42 effector proteins, resulting in increased alcohol and lysine production. Such yeast is well-suited for use commercial alcohol production to increase yields and to increase the value of amino-acid-containing, fermentation product and co-products.

Aspects and embodiments of the compositions and methods are described in the following, independently-numbered paragraphs.

1. In one aspect, modified yeast cells derived from parental yeast cells are provided, the modified cells comprising a genetic alteration that causes the modified cells to produce a decreased amount of functional Cdc42 effector polypeptides compared to the parental cells, wherein the modified cells demonstrate increased alcohol production and/or increased lysine production compared to the parental cells under equivalent fermentation conditions.

2. In some embodiments of the modified cells of paragraph 1, the genetic alteration reduces or prevents the production of functional Gic1 and/or Gic2 polypeptides compared to the parental cells.

3. In some embodiments of the modified cells of paragraph 1, the cells produce a reduced amount, or do not produce a measurable amount of, Gic1 and/or Gic2 polypeptides.

4. In some embodiments of the modified cells of any of paragraphs 1-3, the genetic alteration comprises a disruption of a YHR061c gene, or homolog, thereof, encoding a Gic1 polypeptide and/or disruption of a YDR309c gene, or homolog, thereof, encoding a Gic2 polypeptide, present in the parental cells.

5. In some embodiments of the modified cells of paragraphs 4, the disruption is the result of deletion of all or part of the YHR061c gene, or homolog, thereof, and/or the YDR309c gene, or homolog, thereof, respectively.

6. In some embodiments of the modified cells of paragraphs 4, the disruption is the result of deletion of a portion of genomic DNA comprising the YHR061c gene, or homolog, thereof, and/or the YDR309c gene, or homolog, thereof, respectively.

7. In some embodiments of the modified cells of paragraphs 4, the disruption is the result of mutagenesis of the YHR061c gene, or homolog, thereof, and/or the YDR309c gene, or homolog, thereof, respectively.

8. In some embodiments of the modified cells of any of paragraphs 4-7, disruption of the YHR061c gene, or homolog, thereof, and/or the YDR309c gene, or homolog, thereof, respectively, is performed in combination with introducing a gene of interest at a corresponding genetic locus.

9. In some embodiments of the modified cells of any of paragraphs 1-8, the cells further comprise one or more genes of the phosphoketolase pathway.

10. In some embodiments of the modified cells of paragraph 9, the genes of the phosphoketolase pathway are selected from the group consisting of phosphoketolase, phosphotransacetylase and acetylating acetyl dehydrogenase.

11. In some embodiments of the modified cells of any of paragraphs 1-10, the cells further comprise an exogenous gene encoding a carbohydrate processing enzyme.

12. In some embodiments, the modified cells of any of paragraphs 1-11 further comprise an alteration in the glycerol pathway and/or the acetyl-CoA pathway.

13. In some embodiments, the modified cells of any of paragraphs 1-12 further comprise an alternative pathway for making ethanol.

14. In some embodiments of the modified cells of any of paragraphs 1-13, the cells are of a *Saccharomyces* spp.

15. In another aspect, a method for producing a modified yeast cell is provided, comprising: introducing a genetic alteration into a parental yeast cell, which genetic alteration reduces or prevents the production of functional Cdc42 effector polypeptides compared to the parental cells, thereby producing modified cells that produce during fermentation an increased amount of alcohol and/or lysine compared to the parental cells under equivalent fermentation.

16. In some embodiments of the method of paragraph 15, the genetic alteration reduces or prevents the production of functional Gic1 and/or Gic2 polypeptides compared to the parental cells.

17. In some embodiments of the method of paragraph 15, the cells produce a reduced amount, or do not produce a measurable amount of, Gic1 and/or Gic2 polypeptides.

18. In some embodiments of the method of any of paragraphs 15-17, the genetic alteration comprises a disruption of a YHR061c gene, or homolog, thereof, encoding a Gic1 polypeptide and/or disruption of a YDR309c gene, or homolog, thereof, encoding a Gic2 polypeptide, present in the parental cells.

19. In some embodiments of the method of any of paragraphs 18, the disruption is the result of deletion of all or part of the YHR061c gene, or homolog, thereof, and/or a YDR309c gene, or homolog, thereof, respectively.

20. In some embodiments of the method of any of paragraphs 18, the disruption is the result of deletion of a portion of genomic DNA comprising the YHR061c gene, or homolog, thereof, and/or the YDR309c gene, or homolog, thereof, respectively.

21. In some embodiments of the method of any of paragraphs 18, the disruption is the result of mutagenesis of the YHR061c gene, or homolog, thereof, and/or the YDR309c gene, or homolog, thereof, respectively.

22. In some embodiments of the method of any of paragraphs 18-21, disruption of the YHR061c gene, or homolog, thereof and/or the YDR309c gene, or homolog, thereof, respectively, is performed in combination with introducing a gene of interest at a corresponding genetic locus.

23. In some embodiments of the method of any of paragraphs 15-22, the cells further comprise an exogenous gene encoding a carbohydrate processing enzyme, an alteration in the glycerol pathway, the acetyl-CoA pathway and/or an alternative pathway for making ethanol.

24. In some embodiments of the method of any of paragraphs 15-23, the cells are of a *Saccharomyces* spp.

25. In some embodiments of the method of any of paragraphs 15, the cells are the modified cells of any of paragraphs 1-14.

26. In another aspect, a method for increasing the amount of lysine present in a post-fermentation product is provided, comprising:
   (i) hydrolyzing a starch-containing feedstock with an α-amylase to produce a starch liquefact; (ii) saccharifying the starch liquefact with a glucoamylase to produce glucose; (iii) fermenting the glucose with modified yeast cells derived from parental yeast cells, the modified yeast cells comprising a genetic alteration that causes the production of decreased amounts of functional Cdc42 effector polypeptides compared to the parental cells; and (iv) recovering post-fermentation by-product enriched for lysine compared to post-fermentation by-product recovered from an otherwise identical process using the parental yeast.

27. In some embodiments of the method of paragraph 26, the post-fermentation product is selected from the group consisting of fermentation broth, whole stillage, thin stillage, distillers dried grains, distillers dried grains with solutes, condensed distillers solubles or other protein-containing coproducts.

28. In some embodiments of the method of paragraph 26 or 27, one or more steps (i)-(iv) are combined, simultaneous or over-lapping.

29. In another aspect, a method for increasing the amount of lysine present in a fermentation product is provided, comprising: (i) fermenting glucose or another sugar with modified yeast cells derived from parental yeast cells, the modified yeast cells comprising a genetic alteration that causes the production of decreased amounts of functional Cdc42 effector polypeptides compared to the parental cells; and (ii) recovering fermentation product enriched for lysine compared to a fermentation product recovered from an otherwise identical process using the parental yeast.

30. In some embodiments of the method of any of paragraphs 26-29, the cells are the modified cells of any of paragraphs 1-14.

31. In another aspect, modified yeast cells produced by the method of any of paragraphs 15-25 are provided.

32. In another aspect, a fermentation product produced by the method of any of paragraphs 26-30 is provided.

33. In another aspect, a composition or method having any of the features of paragraphs 1-32 or features mentioned in the description is provided.

These and other aspects and embodiments of present modified cells and methods will be apparent from the description, including the accompanying Figures.

DETAILED DESCRIPTION

I. Overview

Described are methods relating to yeast having a genetic mutation that results in decreased amounts of Cdc42 effector (or target) proteins, resulting in increased alcohol and lysine production. Such yeast is well-suited for use in commercial alcohol production to increase yields and to increase the value of amino-acid-containing, fermentation products and co-products.

II. Definitions

Prior to describing the present strains and methods in detail, the following terms are defined for clarity. Terms not defined should be accorded their ordinary meanings as used in the relevant art.

As used herein, "alcohol" refers to an organic compound in which a hydroxyl functional group (—OH) is bound to a saturated carbon atom.

As used herein, the phrase "degree of polymerization" (DP) refers to the number (n) of anhydroglucopyranose units in a given saccharide. Examples of DP1 are the monosaccharides glucose and fructose. Examples of DP2 are the disaccharides maltose and sucrose. The meaning of DP1, DP12, DP3, DP4, DP4+ etc. is well known in science of carbohydrate processing.

As used herein, "yeast cells" yeast strains, or simply "yeast" refer to organisms from the phyla Ascomycota and Basidiomycota. Exemplary yeast is budding yeast from the order Saccharomycetales. Particular examples of yeast are *Saccharomyces* spp., including but not limited to *S. cerevisiae*. Yeast include organisms used for the production of fuel alcohol as well as organisms used for the production of potable alcohol, including specialty and proprietary yeast strains used to make distinctive-tasting beers, wines, and other fermented beverages.

As used herein, the phrase "variant yeast cells," "modified yeast cells," or similar phrases (see above), refer to yeast that include genetic modifications and characteristics described herein. Variant/modified yeast do not include naturally occurring yeast.

As used herein, the phrase "substantially free of an activity," or similar phrases, means that a specified activity is either undetectable in an admixture or present in an amount that would not interfere with the intended purpose of the admixture.

As used herein, the terms "polypeptide" and "protein" (and their respective plural forms) are used interchangeably to refer to polymers of any length comprising amino acid residues linked by peptide bonds. The conventional one-letter or three-letter codes for amino acid residues are used herein and all sequence are presented from an N-terminal to C-terminal direction. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, functionally and/or structurally similar proteins are considered to be "related proteins." Such proteins can be derived from organisms of different genera and/or species, or even different classes of organisms (e.g., bacteria and fungi). Related proteins also encompass homologs determined by primary sequence analysis, determined by secondary or tertiary structure analysis, or determined by immunological cross-reactivity.

As used herein, the term "homologous protein" refers to a protein that has similar activity and/or structure to a reference protein. It is not intended that homologs necessarily be evolutionarily related. Thus, it is intended that the term encompass the same, similar, or corresponding enzyme(s) (i.e., in terms of structure and function) obtained from different organisms. In some embodiments, it is desirable to identify a homolog that has a quaternary, tertiary and/or primary structure similar to the reference protein. In some embodiments, homologous proteins induce similar immunological response(s) as a reference protein. In some embodiments, homologous proteins are engineered to produce enzymes with desired activity(ies).

The degree of homology between sequences can be determined using any suitable method known in the art (see, e.g., Smith and Waterman (1981) *Adv. Appl. Math.* 2:482; Needleman and Wunsch (1970) *J. Mol. Biol.,* 48:443; Pearson and Lipman (1988) *Proc. Natl. Acad. Sci. USA* 85:2444; programs such as GAP, BESTFIT, FASTA, and TFASTA in the Wisconsin Genetics Software Package (Genetics Computer Group, Madison, WI); and Devereux et al. (1984) *Nucleic Acids Res.* 12:387-95).

For example, PILEUP is a useful program to determine sequence homology levels. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle, (Feng and Doolittle (1987) *J. Mol. Evol.* 35:351-60). The method is similar to that described by Higgins and Sharp ((1989) *CABIOS* 5:151-53). Useful PILEUP parameters including a default gap weight of 3.00, a default gap length weight of 0.10, and weighted end gaps. Another example of a useful algorithm is the BLAST algorithm, described by Altschul et al. ((1990) *J. Mol. Biol.* 215:403-10) and Karlin et al. ((1993) *Proc. Natl. Acad. Sci. USA* 90:5873-87). One particularly useful BLAST program is the WU-BLAST-2 program (see, e.g., Altschul et al. (1996) *Meth. Enzymol.* 266:460-80). Parameters "W," "T," and "X" determine the sensitivity and speed of the alignment. The BLAST program uses as defaults a word-length (W) of 11, the BLOSUM62 scoring matrix (see, e.g., Henikoff and Henikoff (1989) *Proc. Natl. Acad. Sci. USA* 89:10915) alignments (B) of 50, expectation (E) of 10, M'5, N'−4, and a comparison of both strands.

As used herein, the phrases "substantially similar" and "substantially identical," in the context of at least two nucleic acids or polypeptides, typically means that a polynucleotide or polypeptide comprises a sequence that has at least about 70% identity, at least about 75% identity, at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, or even at least about 99% identity, or more, compared to the reference (i.e., wild-type) sequence. Percent sequence identity is calculated using CLUSTAL W algorithm with default parameters. See Thompson et al. (1994) *Nucleic Acids Res.* 22:4673-4680. Default parameters for the CLUSTAL W algorithm are:

Gap opening penalty: 10.0
Gap extension penalty: 0.05
Protein weight matrix: BLOSUM series
DNA weight matrix: IUB
Delay divergent sequences %: 40
Gap separation distance: 8
DNA transitions weight: 0.50
List hydrophilic residues: GPSNDQEKR
Use negative matrix: OFF
Toggle Residue specific penalties: ON
Toggle hydrophilic penalties: ON
Toggle end gap separation penalty OFF.

Another indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

As used herein, the term "gene" is synonymous with the term "allele" in referring to a nucleic acid that encodes and directs the expression of a protein or RNA. Vegetative forms of filamentous fungi are generally haploid, therefore a single copy of a specified gene (i.e., a single allele) is sufficient to confer a specified phenotype.

As used herein, the terms "wild-type" and "native" are used interchangeably and refer to genes proteins or strains found in nature.

As used herein, the term "protein of interest" refers to a polypeptide that is desired to be expressed in modified yeast. Such a protein can be an enzyme, a substrate-binding protein, a surface-active protein, a structural protein, a selectable marker, or the like, and can be expressed at high levels. The protein of interest is encoded by a modified endogenous gene or a heterologous gene (i.e., gene of interest") relative to the parental strain. The protein of interest can be expressed intracellularly or as a secreted protein.

As used herein, "deletion of a gene," refers to its removal from the genome of a host cell. Where a gene includes control elements (e.g., enhancer elements) that are not located immediately adjacent to the coding sequence of a gene, deletion of a gene refers to the deletion of the coding sequence, and optionally adjacent enhancer elements, including but not limited to, for example, promoter and/or terminator sequences, but does not require the deletion of non-adjacent control elements.

As used herein, "disruption of a gene" refers broadly to any genetic or chemical manipulation, i.e., mutation, that substantially prevents a cell from producing a function gene product, e.g., a protein, in a host cell. Exemplary methods of disruption include complete or partial deletion of any portion of a gene, including a polypeptide-coding sequence, a promoter, an enhancer, or another regulatory element, or mutagenesis of the same, where mutagenesis encompasses substitutions, insertions, deletions, inversions, and combinations and variations, thereof, any of which mutations substantially prevent the production of a function gene product. A gene can also be disrupted using RNAi, antisense, or any other method that abolishes gene expression. A gene can be disrupted by deletion or genetic manipulation of non-adjacent control elements.

As used herein, the terms "genetic manipulation" and "genetic alteration" are used interchangeably and refer to the alteration/change of a nucleic acid sequence. The alteration can include but is not limited to a substitution, deletion, insertion or chemical modification of at least one nucleic acid in the nucleic acid sequence.

As used herein, a "primarily genetic determinant" refers to a gene, or genetic manipulation thereof, that is necessary and sufficient to confer a specified phenotype in the absence of other genes, or genetic manipulations, thereof. However, that a particular gene is necessary and sufficient to confer a specified phenotype does not exclude the possibility that additional effects to the phenotype can be achieved by further genetic manipulations.

As used herein, a "functional polypeptide/protein" is a protein that possesses an activity, such as an enzymatic activity, a binding activity, a surface-active property, or the like, and which has not been mutagenized, truncated, or otherwise modified to abolish or reduce that activity. Functional polypeptides can be thermostable or thermolabile, as specified.

As used herein, "a functional gene" is a gene capable of being used by cellular components to produce an active gene product, typically a protein. Functional genes are the antithesis of disrupted genes, which are modified such that they cannot be used by cellular components to produce an active gene product, or have a reduced ability to be used by cellular components to produce an active gene product.

As used herein, yeast cells have been "modified to prevent the production of a specified protein" if they have been genetically or chemically altered to prevent the production of a functional protein/polypeptide that exhibits an activity characteristic of the wild-type protein. Such modifications include, but are not limited to, deletion or disruption of the gene encoding the protein (as described, herein), modification of the gene such that the encoded polypeptide lacks the aforementioned activity, modification of the gene to affect post-translational processing or stability, and combinations, thereof.

As used herein, "fermentation broth" is the product of an ethanol production facility following fermentation with yeast but prior to distillation.

As used herein, "whole stillage" is the byproduct an ethanol production facility following distillation.

As used herein, "thin stillage" is the liquid portion of whole stillage following separation of solid materials.

As used herein, "distillers' grains (DG)" is the solid/slurry component of whole stillage.

As used herein, "distillers' dried grains (DDG) is DG that have been dried.

As used herein, "distillers' dried grains with solutes (DDGS) is DG that has been dried along with the concentrated thin stillage for added nutritional value.

As used herein, a "wet" by-product of distillation contains at least 20% water by weight.

As used herein, a "dried" by-product of distillation contains less than 20% water by weight.

As used herein, "aerobic fermentation" refers to growth in the presence of oxygen.

As used herein. "anaerobic fermentation" refers to growth in the absence of oxygen.

As used herein, the singular articles "a," "an," and "the" encompass the plural referents unless the context clearly dictates otherwise. All references cited herein are hereby incorporated by reference in their entirety. The following abbreviations/acronyms have the following meanings unless otherwise specified:

° C. degrees Centigrade
DG distillers' grains
DDG distillers' dried grains
DDGS distillers' dried grains with solutes
DNA deoxyribonucleic acid
DP degree of polymerization
DS dry solids
EtOH ethanol
g or gm gram
g/L grams per liter
GA glucoamylase
GAU/g DS glucoamylase units per gram dry solids
HPLC high performance liquid chromatography
hr or h hour
kDa kilodalton
M molar
mg milligram
mL or ml milliliter
ml/min milliliter per minute
mM millimolar
N normal
Na not applicable
PCR polymerase chain reaction
ppm parts per million
SAPU/g DS protease units per gram dry solids
SSCU/g DS fungal α-amylase units per gram dry solids
Δ relating to a deletion
μg microgram
μL and μl microliter
μM and μm micromolar

III. Modified Yeast Cells Expressing Reduced Levels of Cdc42 Target Polypeptides Cdc42 is Rho-family GTPase that functions as a master regulator of cytoskeleton remodeling in many cell types, including budding yeast. Activated Cdc42 concentrates in a region of the cell cortex, where it recruits effector proteins to remodel the cytoskeleton in a polarized manner. At least in yeast cells, polarization involves a positive feedback loop, in which effectors, including those referred to as p21-activated kinases (PAK), recruit a guanine nucleotide exchange factor (GEF), resulting in a further local increase of GTP-Cdc42 concentration. Additional effector proteins include Gic1 and Gic2, which are implicated in regulation of the actin and septin cytoskeleton.

Applicants have discovered that yeast having a genetic alteration that decreases Gic1 or Gic2 production demonstrate increased ethanol production in fermentations, compared to otherwise identical yeast. Moreover, applicants have discovered that yeast having such a genetic alteration demonstrate increased lysine production in fermentations, compared to otherwise identical yeast.

Reduction in the amount of functional Gic polypeptides can result from disruption of a gene encoding the Gic1 polypeptide (eg, YHR061c) and/or a gene encoding the Gic2 polypeptide (eg, YDR309c) in Saccharomyces cerevisiae. Because disruption of a gene encoding a Gic polypeptide is a primary genetic determinant for conferring the altered alcohol and lysine production phenotype to the modified cells, in some embodiments the modified cells need only understand such a disrupted gene, while all other genes can remain intact. In other embodiments, the modified cells can optionally include additional genetic alterations compared to the parental cells from which they are derived. While such additional genetic alterations are not necessary to confer the described phenotype, they may confer other advantages to the modified cells.

Disruption of a gene encoding a Gic polypeptide can be performed using any suitable methods that substantially prevent expression of functional Gic polypeptides. Exemplary methods of disruption as are known to one of skill in the art include but are not limited to: complete or partial deletion of a gene encoding a Gic polypeptide, including complete or partial deletion of, e.g., a Gic-coding sequence, the promoter, the terminator, an enhancer, or another regulatory element; and complete or partial deletion of a portion of the chromosome that includes any portion of a gene encoding a Gic polypeptide. Particular methods of disrupting a gene encoding a Gic polypeptide gene include making nucleotide substitutions or insertions in any portion of such a gene, e.g., a gene encoding a Gic polypeptide-coding sequence, the promoter, the terminator, an enhancer, or another regulatory element.

Mutations in a gene encoding a Gic polypeptide can reduce the efficiency of a promoter, reduce the efficiency of an enhancer, interfere with the splicing or editing of a mRNA, interfere with the translation of a mRNA, introduce a stop codon into a Gic-coding sequence to prevent the translation of full-length Gic protein, change the coding sequence of a Gic protein to produce a less active or inactive protein or reduce Gic interaction with other proteins, or DNA, change the coding sequence of a Gic protein to produce a less stable protein or target the protein for destruction, cause a Gic protein to misfold or be incorrectly modified (e.g., by glycosylation), or interfere with cellular trafficking of a Gic protein. In some embodiments, these and other genetic manipulations act to reduce or prevent the expression of a functional Gic protein, or reduce or prevent the normal function of Gic1 or Gic2.

Preferably, disruption of a gene encoding a Gic polypeptide is performed by genetic manipulation using sequence-specific molecular biology techniques, as opposed to chemical mutagenesis, which is generally not targeted to specific nucleic acid sequences. However, chemical mutagenesis is not excluded as a method for making modified yeast cells.

The exemplary Gic1 polypeptide described, herein, is represented by Genbank Accession No. NP_011928 and SEQ ID NO: 2, below:

```
MTEGKRLQQM ELPQMKSIWI DEDQEMEKLY GFQVRQRFMN

GPSTDSDEDA DEDLGIVLVD SKKLALPNKN NIKLPPLPNY

MTINPNINSN HKSLTNKKKN FLGMFKKKDL LSRRHGSAKT

AKQSSISTPF DFHHISHANG KREDNPLESH EEKHDVESLV

KFTSLAPQPR PDSNVSSKYS NVVMNDSSRI VSSSTIATTM

DSHHDGNETN NTPNGNKQLD SPTDLEMTLE DLRNYTFPSV

LGDSVSEKTN PSSPSVSSFS GKFKPRELSA LHTPELGNCF

NVDQSLNSPG NRISVDDVLK FYYQCSETST PRNT
```

The exemplary Gic2 polypeptide described, herein, is represented by Genbank Accession No. NP_010595 and SEQ ID NO: 2, below:

```
MTSASITNTG NETMNLPQMR SIWLDEDEEA EKLYGLQAQQ

FMGSDDEENL GITFINSDKP VLSNKKNIEL PPLSPNSHPS

CHHRRSNSNS AKSKESSSSS SSANKTNHKK VFLKLNLLKK

KLLGAQPDIR GKGISTPFDF QHISHADTRN GFQDEQLQEP

SSLSTEIKDD YTSSSSKRDS KSLNKAFVTE RIPANRESKL

ISRSHENKTS RLSVARSISV TSSNYSKNTQ GNNHSINGRV

VSTSTMATSI FEYSPNASPK QFKNKSHALG HRYTNSTDSS

ESSLDFLKNY NFPTLLEDKP ILDFLPRSQR SSAYRSLLET

PNSNKDSAKA FFPSRQSPLP KRRNSIATPS PQSKFSYSDS

PVNHRKSFDD VLYSFNQLEP LQT
```

It is expected that the present compositions and methods are applicable to other structurally similar Gic polypeptides, as well as other related proteins, homologs, and functionally similar polypeptides.

In some embodiments of the present compositions and methods, the amino acid sequence of the Gic protein that is altered in production levels has a specified degree of overall amino acid sequence identity to the amino acid sequence of SEQ ID NO: 1 or 2, e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99% identity, to SEQ ID NO: 1 or 2.

In some embodiments of the present compositions and methods, the gene encoding a Gic polypeptide that is disrupted encodes a Gic protein that has a specified degree of overall amino acid sequence identity to the amino acid sequence of SEQ ID NO: 1 or 2, e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99% identity, to SEQ ID NO: 1 or 2.

In some embodiments of the present compositions and methods, the gene encoding a Gic polypeptide that is disrupted is YDR309c (SEQ ID NO: 3, infra), which encodes Gic2. In some embodiments, the gene encoding a Gic polypeptide that is disrupted is YHR061c (SEQ ID NO: 4, infra), which encodes Gic1. In some embodiments the gene encoding a Gic polypeptide that is disrupted has a specified degree of overall amino acid sequence identity to the nucleic acid sequence of SEQ ID NO: 3 or 4, e.g., at least about 70%, at least about 75%, at least about 80%, at least about 85%, at least about 90%1, at least about 91%, at least about 92%, at least about 93%, at least about 94%, at least about 95%, at least about 96%, at least about 97%, at least about 98%, or even at least about 99% identity, to SEQ ID NO: 3 or 4.

The amino acid and nucleic acid sequence information provided, herein, readily allows the skilled person to identify a Gic protein, and the nucleic acid sequence encoding a Gic protein, in any yeast, and to make appropriate disruptions in a gene encoding a Gic polypeptide to affect the production of the Gic protein.

In some embodiments, the decrease in the amount of functional Gic1 and/or Gic2 polypeptide in the modified cells is a decrease of at least 30%, at least 40%, at least 50%, at least 60%, at least 70%, at least 80%, at least 90%, at least 95%, at least 98%, at least 99%, or more, compared to the amount of functional Gic polypeptide in parental cells growing under the same conditions. In some embodiments, the reduction of expression of functional Gic1 and/or Gic2 protein in the modified cells is a reduction of at least 30%, at least 40%, at least 50%, at least 60%, at least 70%, at least 80%, at least 90%, at least 95%, at least 98%, at least 99%, or more, compared to the amount of functional Gic polypeptide in parental cells growing under the same conditions.

In some embodiments, the increase in alcohol production by the modified cells is an increase of at least 1%, at least 1.5%, at least 2%, at least 2.5%, at least 3%, at least 3.5%, at least 4%, at least 4.5%, at least 5%, or more, compared to the amount of alcohol produced in parental cells growing under the same conditions.

In some embodiments, the increase in lysine production by the modified cells is an increase of at least 1.1-fold, at least 1.2-fold, at least 1.3-fold, at least 1.4-fold, at least 1.4-fold, at least 1.5-fold, at least 1.6-fold, at least 1.7-fold, at least 1.8-fold, at least 1.9-fold or even at least 2-fold, or more, compared to the amount of lysine produced in parental cells growing under the same conditions. In particular embodiments, the increase is under high-DS conditions.

In some embodiments, the parental cell that is modified already includes a gene of interest, such as a gene encoding a selectable marker, carbohydrate-processing enzyme, or other polypeptide. In some embodiments, a gene of interest is subsequently introduced into the modified cells.

In some embodiments, the modified cells include other genes or other modifications that increase lysine production.

IV. Combination of Decreased Cdc42 Effectors with Other Mutations that Affect Alcohol Production In some embodiments, in addition to expressing decreased amounts of Cdc42 effector polypeptides, the present modified yeast cells further include additional modifications that affect alcohol production.

In particular embodiments the modified yeast cells include an artificial or alternative ethanol-producing pathway resulting from the introduction of a heterologous phosphoketolase (PKL) gene, a heterologous phosphotransacetylase (PTA) gene and a heterologous acetylating acetyl dehydrogenase (AADH), as described in WO2015148272 (Miasnikov et al.), to channel carbon flux away from the glycerol pathway and toward the synthesis of acetyl-CoA, which is then converted to ethanol.

The modified cells may further include mutations that result in attenuation of the native glycerol biosynthesis pathway, which are known to increase alcohol production. Methods for attenuation of the glycerol biosynthesis pathway in yeast are known and include reduction or elimination of endogenous NAD-dependent glycerol 3-phosphate dehydrogenase (GPD) or glycerol phosphate phosphatase activity (GPP), for example by disruption of one or more of the genes GPD1, GPD2, GPP1 and/or GPP2. See, e.g., U.S. Pat. No. 9,175,270 (Elke et al.), U.S. Pat. No. 8,795,998 (Pronk et al.) and U.S. Pat. No. 8,956,851 (Argyros et al.).

The modified yeast may further feature increased acetyl-CoA synthase (also referred to acetyl-CoA ligase) activity (EC 6.2.1.1) to scavenge (ie, capture) acetate produced by chemical or enzymatic hydrolysis of acetyl-phosphate (or present in the culture medium of the yeast for any other reason) and converts it to Ac-COA. This avoids the undesirable effect of acetate on the growth of yeast cells and may further contribute to an improvement in alcohol yield. Increasing acetyl-CoA synthase activity may be accomplished by introducing a heterologous acetyl-CoA synthase gene into cells, increasing the expression of an endogenous acetyl-CoA synthase gene and the like. A particularly useful acetyl-CoA synthase for introduction into cells can be obtained from *Methanosaeta concilii* (UniProt/TrEMBL Accession No.: WP_013718460). Homologs of these enzymes, including enzymes having at least 85%, at least 90%, at least 92%, at least 95%, at least 97%, at least 98% and even at least 99% amino acid sequence identity to the aforementioned acetyl-CoA synthase from *Methanosaeta concilii*, are also useful in the present compositions and methods.

In some embodiments the modified cells may further include a heterologous gene encoding a protein with $NAD^+$-dependent acetylating acetaldehyde dehydrogenase activity and/or a heterologous gene encoding a pyruvate-formate lyase. The introduction of such genes in combination with attenuation of the glycerol pathway is described, e.g., in U.S. Pat. No. 8,795,998 (Pronk et al.).

In some embodiments, the present modified yeast cells may further overexpress a sugar transporter-like (STL1) polypeptide (see, e.g., Ferreira et al. (2005) *Mol Biol Cell* 16:2068-76; Dušková et al. (2015) *Mol Microbiol* 97:541-59 and WO 2015023989 A1) to increase ethanol production and reduce acetate.

In some embodiments, the present modified yeast cells may further overexpress a polyadenylate-binding protein, e.g., PAB1, to increase alcohol production and reduce acetate production.

In some embodiments, the present modified yeast cells further comprise a butanol biosynthetic pathway. In some embodiments, the butanol biosynthetic pathway is an isobutanol biosynthetic pathway. In some embodiments, the isobutanol biosynthetic pathway comprises a polynucleotide encoding a polypeptide that catalyzes a substrate to product conversion selected from the group consisting of: (a) pyruvate to acetolactate; (b) acetolactate to 2,3-dihydroxyisovalerate; (c) 2,3-dihydroxyisovalerate to 2-ketoisovalerate; (d) 2-ketoisovalerate to isobutyraldehyde; and (e) isobutyraldehyde to isobutanol. In some embodiments, the isobutanol biosynthetic pathway comprises polynucleotides encoding polypeptides having acetolactate synthase, keto acid reductoisomerase, dihydroxy acid dehydratase, ketoisovalerate decarboxylase, and alcohol dehydrogenase activity.

In some embodiments, the modified yeast cells comprising a butanol biosynthetic pathway further comprise a modification in a polynucleotide encoding a polypeptide having pyruvate decarboxylase activity. In some embodiments, the yeast cells comprise a deletion, mutation, and/or substitution in an endogenous polynucleotide encoding a polypeptide having pyruvate decarboxylase activity. In some embodiments, the polypeptide having pyruvate decarboxylase activity is selected from the group consisting of: PDC1, PDC5, PDC6, and combinations thereof. In some embodiments, the yeast cells further comprise a deletion, mutation, and/or substitution in one or more endogenous polynucleotides encoding FRA2, ALD6, ADH1, GPD2, BDH1, and YMR226C.

V. Combination of Decreased Cdc42 Effectors with Other Beneficial Mutations

In some embodiments, in addition to expressing reduced amounts of Cdc42 effector polypeptides, optionally in combination with other genetic modifications that benefit alcohol production, the present modified yeast cells further include any number of additional genes of interest encoding proteins of interest. Additional genes of interest may be introduced before, during, or after genetic manipulations that result in reduced expression of Cdc42 effector polypeptides. Proteins of interest, include selectable markers, carbohydrate-processing enzymes, and other commercially-relevant polypeptides, including but not limited to an enzyme selected from the group consisting of a dehydrogenase, a transketolase, a phosphoketolase, a transaldolase, an epimerase, a phytase, a xylanase, a β-glucanase, a phosphatase, a protease, an α-amylase, a β-amylase, a glucoamylase, a pullulanase, an isoamylase, a cellulase, a trehalase, a lipase, a pectinase, a polyesterase, a cutinase, an oxidase, a transferase, a reductase, a hemicellulase, a mannanase, an esterase, an isomerase, a pectinases, a lactase, a peroxidase and a laccase. Proteins of interest may be secreted, glycosylated, and otherwise-modified.

VI. Yeast Cells Suitable for Modification

Yeasts are unicellular eukaryotic microorganisms classified as members of the fungus kingdom and include organisms from the phyla Ascomycota and Basidiomycota. Yeast that can be used for alcohol production include, but are not limited to, *Saccharomyces* spp., including *S. cerevisiae*, as well as *Kluyveromyces, Lachancea* and *Schizosaccharomyces* spp. Numerous yeast strains are commercially available, many of which have been selected or genetically engineered for desired characteristics, such as high alcohol production, rapid growth rate, and the like. Some yeasts have been genetically engineered to produce heterologous enzymes, such as glucoamylase or α-amylase.

VII. Substrates and Conditions

Alcohol production from a number of carbohydrate substrates, including but not limited to corn starch, sugar cane, cassava, and molasses, is well known, as are innumerable variations and improvements to enzymatic and chemical conditions and mechanical processes. The present compositions and methods are believed to be fully compatible with such substrates and conditions.

Numerous variations of ethanol production process exist, including cold cook, or no cook, involving liquefaction at or below the gelatinization temperature, simultaneous saccharification and fermentation, fractionation processes, and the like. None are expected to be incompatible with the present compositions and methods.

VII. Fermentation Products and Co-Products

Typical alcohol fermentation products include organic compound having a hydroxyl functional group (—OH) is bound to a carbon atom. Exemplary alcohols include but are not limited to methanol, ethanol, n-propanol, isopropanol, n-butanol, isobutanol, n-pentanol, 2-pentanol, isopentanol, and higher alcohols. The most commonly made fuel alcohols are ethanol, and butanol. Using the present modified yeast, an increase of at least 1%, at least 1.5%, at least 2%, at least 2.5%, at least 3%, at least 3.5%, at least 4%, at least 4.5%, at least 5%, or more, can be realized.

Valuable by-products (or co-products) of alcohol production, and particularly dry-grind ethanol production, are products for animal feed, usually in the form of distillers' dried grains (DDG) or, more commonly, distillers' dried grains with solutes (DDGS). Such animal feed products are in many ways more nutritional than the initial feed-stocks used for ethanol production as they are depleted for carbohydrates but enriched for amino acids derived both from the feedstock and the fermenting organism (i.e., ethanologen).

The specific amino acid composition of DDGS or other corn co-product is important to the quality of animal feed as some amino acids are far more important than others. Lysine is an essential amino acid for most farm animals and, if not provided in adequate amounts by adequately by DDG, DDGS, or other post fermentation co-products, must be supplemented to maximize feed conversion. Synthetic lysine is expensive and represents a significant cost of animal feed.

Because yeast can represent a significant component of post-fermentation products, the amino acid content of the yeast may significantly affect the amino acid content of fermentation broth, whole stillage, thin stillage, distillers dried grains, distillers dried grains with solutes, condensed distillers solubles or other protein-containing post fermentation coproducts. Replacing convention yeast with the present yeast increases the amounts of lysine in such post-fermentation products, thereby increasing their value as animal feed products. Using the present modified yeast, an increase in lysine of at least 1.1-fold, at least 1.2-fold, at least 1.3-fold, at least 1.4-fold, at least 1.4-fold, at least 1.5-fold, at least 1.6-fold, at least 1.7-fold, at least 1.8-fold, at least 1.9-fold or even at least 2-fold, or more, can be realized.

These and other aspects and embodiments of the present strains and methods will be apparent to the skilled person in view of the present description. The following examples are intended to further illustrate, but not limit, the strains and methods.

EXAMPLES

Example 1: Deletion of Gic2 in Yeast

Using standard molecular biology techniques, the YDR309c gene was disrupted by deleting essentially the entire coding sequence for Gic2 in FERMAX™ Gold (Martrex, Inc., Chaska, MN, USA, herein "FG"), a commercially available strain of *Saccharomyces cerevisiae* used for large-scale ethanol production. All procedures were based on the publicly available nucleic acid sequence of YDR309c, which is provided below as SEQ ID NO: 3; 9SGDID: S000002717; chrIV:1079048 . . . 1080199; the corresponding Gic2 effector polypeptide is represented, supra, as SEQ ID NO: 2):

ATGACTAGTGCAAGTATTACCAATACTGGAAACGAAACCATGAACCTTCC

ACAGATGCGGTCGATTTGGCTGGATGAAGATGAAGAAGCTGAAAAACTCT

ACGGTCTGCAGGCCCAGCAATTCATGGGATCTGATGATGAAGAAAACCTA

GGCATTACTTTCATCAACAGCGATAAACCTGTGCTGAGTAACAAGAAAAA

CATTGAGTTGCCTCCACTTTCACCAAATTCACATCCGTCTTGCCACCACA

GGAGAAGTAATTCTAACTCTGCAAAGTCTAAAGAATCATCGTCATCATCG

TCCAGCGCCAACAAGACAAATCACAAAAAGGTTTTCCTTAAGCTTAATTT

GTTGAAGAAAAAGTTGCTTGGTGCCCAACCGGACATAAGAGGTAAAGGTA

TCTCCACACCATTTGATTTTCAACATATTTCACATGCTGACACTAGAAAT

GGATTCCAAGATGAGCAATTGCAGGAACCTTCATCGCTGTCCACAGAGAT

TAAGGACGACTATACCTCCTCCTCAAGCAAGCGGGATTCGAAATCACTAA

ATAAAGCTTTTGTCACTGAAAGGATCCCTGCTAATCGTGAAAGCAAACTC

ATTTCAAGATCGCACGAAAATAAGACATCAAGACTATCAGTCGCGCGTTC

GATCTCAGTAACGTCCTCCAATTACTCTAAAAACACACAAGGAAACAATC

ATTCCATTAATGGGAGAGTCGTATCTACGTCAACTATGGCTACATCTATT

TTTGAGTATTCCCCAAACGCATCTCCAAAACAATTTAAAAATAAGTCACA

CGCTCTGGGTCATAGATACACTAATTCCACGGATTCTAGTGAGTCTTCGC

TGGATTTTTTGAAGAACTACAACTTCCCCACACTACTTGAAGATAAGCCT

ATTTTAGACTTCTTGCCTCGTTCTCAGAGGTCAAGCGCTTATCGTAGCCT

TTTAGAGACCCCAAACTCAAATAAGGACTCAGCAAAAGCCTTCTTTCCTT

CACGCCAAAGCCCTCTTCCCAAGAGAAGAAACTCTATAGCTACGCCTTCT

CCACAATCTAAATTTTCCTACTCTGACTCCCCTGTAAACCATAGAAAATC

TTTCGATGATGTTCTTTATTCTTTCAACCAGCTCGAGCCCCTGCAAACTT

AA

Deletion of the Gic2 gene was confirmed by colony PCR. The modified yeast was grown in non-selective media to remove the plasmid conferring kanamycin resistance used to select transformants, resulting in modified yeast that required no growth supplements compared to the parental yeast. One modified strain, designated FG-Gic2 was selected for further study.

Example 2: Deletion of Gic1 in Yeast

Using standard molecular biology techniques, the YHR061c gene was disrupted by deleting essentially the entire coding sequence for Gic1 in FG. All procedures were based on the publicly available nucleic acid sequence of YHR061c, which is provided below as SEQ ID NO: 4; SGDID:S000001103; chrVIII:221534 . . . 222478; the corresponding Gic1 effector polypeptide is represented, supra, as SEQ ID NO: 1):

ATGACTGAAGGAAAGAGGCTGCAACAGATGGAGCTTCCTCAAATGAAATC

CATTTGGATTGACGAGGATCAGGAAATGGAAAAATTGTATGGATTCCAAG

TAAGGCAACGATTCATGAATGGACCTAGTACGGATTCCGATGAAGACGCC

GACGAAGATTTAGGAATTGTTCTCGTTGACAGTAAAAAGCTGGCTTTGCC

GAACAAGAACAACATCAAATTGCCCCCTTTGCCCAATTACATGACGATCA

ACCCTAACATAAATTCCAATCACAAGTCATTAACTAATAAAAAGAAGAAT

TTCCTGGGCATGTTCAAAAAAAGGACCTGTTGTCGAGGAGACATGGGTC

TGCCAAAACCGCAAAACAGTCAAGTATATCTACACCATTTGATTTTCACC

ATATTTCGCATGCTAATGGTAAAAGGGAAGACAACCCTCTTGAGTCGCAC

GAAGAAAAACATGATGTAGAATCATTAGTCAAATTCACGTCTTTGGCACC

GCAACCCCGACCAGATTCAAACGTCTCTTCTAAATATTCCAATGTTGTGA

TGAACGATTCGAGCAGAATAGTGTCTTCCTCCACAATAGCTACAACGATG

GATTCTCACCACGATGGTAACGAAACCAACAATACCCCAAATGGCAATAA

GCAATTAGACTCGCCTACAGATTTGGAAATGACCTTGGAAGACTTGAGAA

ATTATACATTTCCTTCTGTTCTTGGAGATAGCGTCAGCGAAAAGACCAAT

CCTTCCTCTCCCTCTGTTTCATCATTTTCTGGCAAATTCAAGCCAAGAGA

GTTGAGTGCGCTACATACGCCCGAATTAGGAAATTGTTTCAATGTAGATC

AGTCGCTAAATTCCCCTGGTAACAGAATATCTGTGGATGACGTGCTAAAA

TTCTACTATCAATGTAGTGAAACTAGTACTCCTCGAAATACCTGA

Deletion of the Gic1 gene was confirmed by colony PCR and the modified yeast was grown in non-selective media to remove the plasmid conferring kanamycin resistance used to select transformants, resulting in modified yeast that required no growth supplements compared to the parental yeast. One modified strain, designated FG-Gic1 was selected for further study.

Example 3: Ethanol Production by Modified Yeast at a Single Temperature

FG-Gic2 and FG-Gic1 yeast were tested for their ability to produce ethanol compared to the FG benchmark yeast (which is wild-type for both genes) in liquefact at 32° C. Liquefact (i.e., corn flour slurry having a dry solid (DS) value of 33% was prepared by adding 600 ppm urea, 0.124 SAPU/g DS FERMGEN™ 2.5× (an acid fungal protease), 0.33 GAU/g DS variant *Trichoderma reesei* glucoamylase and 1.46 SSCU/g DS *Aspergillus kawachii* α-amylase at pH 4.8.

50 grams of liquefact was weighted into 100 ml vessels and inoculated with fresh overnight cultures from colonies of the modified strain or FG strain at 32° C. Samples were harvested at 55.2 hr by centrifugation, filtered through 0.2 µm filters, and analyzed for ethanol, glucose, acetate and glycerol content by HPLC (Agilent Technologies 1200 series) using Bio-Rad Aminex HPX-87H columns at 55° C. with an isocratic flow rate of 0.6 ml/min in 0.01 N $H_2SO_4$ eluent (all numbers are in g/L unless otherwise indicated). A 2.5 µl sample injection volume was used. Calibration standards used for quantification included known amounts of DP4+, DP3, DP2, DP1, glycerol and ethanol. The results of the analyses are shown in Table 1. Ethanol increase is reported with reference to the FG strain.

TABLE 1

Analysis of fermentation broth after fermentation after 55 hours at 32° C.

| Strain | DP2 | DP3 | DP4+ | Glucose | Glycerol | Acetate | EtOH | Fold increase |
|---|---|---|---|---|---|---|---|---|
| FG | 3.14 | 1.27 | 6 | 0.53 | 13.74 | 0.76 | 139.26 | 0 |
| FG-Gic2 | 3.24 | 1.3 | 6.08 | 0.51 | 13.52 | 0.7 | 140.83 | 1.011 |
| FG-Gic1 | 3.26 | 1.29 | 6.07 | 0.56 | 13.9 | 073 | 140.45 | 1.009 |

Yeast harboring disrupted Gic1 or Gic2 genes produced about a 1% increase in ethanol compared the unmodified FG reference strains at 32° C.

Example 4: Ethanol Production by Modified Yeast Under Ramping Temperatures

FG-Gic2 and FG-Gic1 yeast were tested for their ability to produce ethanol compared to benchmark FG yeast (wild-type for both genes) in liquefact in a 35° C. ramp. Liquefact (as above) was weighted into 100 ml vessels and inoculated with fresh overnight cultures from colonies of the modified strain or FG strain using 35° C. ramp conditions as summarized in Table 2. Samples were harvested by centrifugation after 55.2 hr, filtered through 0.2 μm filters, and analyzed as above for ethanol, glucose, acetate and glycerol content by HPLC. The results of the analyses are shown in Table 3. Ethanol increase is reported with reference to the FG strain.

TABLE 2

Temperature ramp condition

| Time (hour) | Temperature (° C.) |
|---|---|
| 0-10 | 32.0 |
| 10-12 | 33.0 |
| 12-15 | 34.0 |
| 15-17 | 35.0 |
| 17-22 | 35.5 |
| 22-27 | 34.5 |
| 27-31 | 34.0 |
| 31-36 | 33.5 |
| 36-41 | 33.0 |
| 41-55 | 32.5 |
| 55-end | 32.0 |

TABLE 3

Analysis of fermentation broth following fermentation under ramping conditions

| Strain | DP2 | DP3 | DP4+ | Glucose | Glycerol | Acetate | EtOH | Fold increase |
|---|---|---|---|---|---|---|---|---|
| FG | 3.87 | 1.43 | 5.87 | 18.32 | 14.24 | 0.93 | 128.96 | 0 |
| FG-Gic2 | 4.28 | 1.46 | 5.86 | 8.93 | 13.74 | 0.97 | 133.64 | 1.036 |
| FG-Gic1 | 4.37 | 1.46 | 5.89 | 10.47 | 14.02 | 1.02 | 132.89 | 1.030 |

As shown in Table 3, yeast harboring the Gic1 or Gic2 deletions produced about 3.0 to 3.6% more ethanol compared the unmodified reference strains at 35° C. ramp.

Example 5: Ethanol Production by Modified Yeast Under High-DS Conditions

FG-Gic2 and FG-Gic1 yeast were tested for their ability to produce ethanol compared to benchmark FG yeast in high-DS (i.e., 35%) liquefact conditions at 32° C. Liquefact was prepared and analyzed as above. The results of analysis are shown in Table 4. Ethanol increase is reported with reference to the FG strain.

TABLE 4

Analysis of fermentation broth following fermentation under high-DS conditions

| Strain | DP2 | DP3, | DP4+ | Glucose | Glycerol | Acetate | EtOH | Fold increase | EtOH/DS |
|---|---|---|---|---|---|---|---|---|---|
| FG | 4.41 | 1.69 | 6.87 | 2023 | 16.82 | 1.04 | 141.71 | 0 | 4.05 |
| FG-Gic2 | 4.50 | 1.73 | 6.80 | 6.66 | 16.58 | 1.10 | 148.85 | 1.050 | 4.25 |
| FG Gic1 | 4.57 | 1.73 | 6.81 | 7.59 | 16.77 | 1.10 | 148.05 | 1.045 | 4.23 |

As shown in Table 4, yeast harboring the Gic2 or Gic1 gene deletion produced about 4.5 to 5% more ethanol compared the unmodified reference strains at 35% DS.

Example 6: Lysine Content in Fermentation End Products Using Modified Yeast

The intracellular free lysine content of FG-Gic2 and FG-Gic1 yeast were tested and compared to benchmark FG yeast (wild-type for both genes) after 24 hrs growth in minimum media. Intracellular metabolites from cell pellet were extracted using standard amino acid extraction conditions with a 60% methanol solution Villas-Boas, S. G. et al., (2005) *Biochem J.* 388:669-77, and the samples processed using HPLC. Samples were analyzed for L-lysine content following derivatization using o-phthalaldehyde. Derivatized L-lysine was detected by HPLC (Agilent Technologies 1260) using an Eclipse Plus C18 column (4.6×150 mm, 3.5-Micron) at 40° C. in a gradient of phosphate buffer, pH 7.8 and acetonitrile:methanol:water (45:45:10). Calibration standards used for quantification included known amounts L-lysine or an amino acid standard mixture (Agilent Technologies) including L-lysine.

As shown in Table 5, yeast-harboring mutations in produced 1.3 to 1.67-fold more free intracellular lysine compared to the unmodified reference strain.

TABLE 5

Intracellular free lysine in modified and unmodified cells

| Strain | Intracellular free lysine (mM) | Fold increase over FG |
|---|---|---|
| FG | 0.91 | na |
| FG-Gic2 | 1.18 | 1.3 |
| FG-Gic1 | 1.52 | 1.67 |

Example 7: Bioavailable Lysine Content of Fermentation Co-Products Using Modified Yeast The total lysine content of fermentation co-products was tested for using FG-Gic2 and the benchmark strain. Liquefact (corn mash slurry) was prepared by adding 600 ppm of urea, 0.124 SAPU/g ds acid fungal protease, 0.33 GAU/g ds variant *Trichoderma reesei* glucoamylase and 1.46 SSCU/g ds *Aspergillus kawachii* α-amylase, adjusted to a pH of 4.8 with sulfuric acid, 100 g of prepared corn liquefact was subjected to fermentation with either FG-Gic2 or the benchmark FG strain at 32'C with shaking at 200 rpm. After 67 hours, the fermentation broth from duplicate fermentation flasks was collected in an 800-mL beaker and placed into a shaking water bath at 95° C. to evaporate off the ethanol. The fermentation broth was allowed to incubate for approximately 3-5 hours until no significant ethanol was detected by HPLC.

The resulting material (i.e., whole stillage) was spun down at 6,000 rpm for 10 min. The supernatant (i.e., thin stillage) and precipitate (i.e., wet cake) were both collected. Wet cake was dried at 37'C until reaching a dry solids content of about 34-35%. Thin stillage was weighed into 600 mL beakers and put in a shaking water bath at 97° C. to concentrate the contents by about 5-fold (by weight) to create syrup.

To make fermentation co-products similar to DDGS samples, wet cake and the corresponding syrup were combined at a 2-to-1 mass ratio (as-is weights) and mixed well. DDGS was spread onto a metal tray and dried in a 99° C. oven for about 3 hours, with occasional mixing to >90% dry solids content.

To test for bioavailable amino acids, samples of DDGS were incubated with pepsin and pancreatin, based on a previously reported method (Qiao, Y (2001) *Routine techniques for monitoring the nutritional value of animal meals*, Doctoral thesis at North Carolina State University). Briefly, 0.33 g of DDGS was added to a 20 mL scintillation vial along with 3.33 mL of 0.05 M citrate buffer (pH 2) and approximately 0.012 g pepsin (from porcine gastric mucosa) at ≥400 units/mg protein. The mixture was allowed to incubate at 38'C for about 24 hours with shaking at 200 rpm. After this time, 5 mL of phosphate buffer (0.2 M, pH 11.5, with 0.025% w/w sodium azide) and approximately 0.023 g pancreatin (from porcine pancreas, 4×UXP specifications) was added to each vial. The vials were placed back into the 38'C incubator shaking with at 200 rpm for around 66 hours. After this time, samples were taken from each vial, spun down through a 0.2 µM filter and analyzed by HPLC for free amino acids.

The results shown in Table 6 compare the measured bioavailable lysine content in the fermentation co-product produced with the FG-Gic2 strains and the FG benchmark. As shown, a 19% increase in co-product bioavailable lysine was observed for using FG-Gic2 strain.

TABLE 5

Lysine in fermentation co-product produced by modified and unmodified cells

| Strain | Lysine (% dry weight) | Fold increase |
|---|---|---|
| FG | 0.91 | na |
| FG-Gic2 | 1.08 | 1.19 |

Similar results were obtained using yeast harboring an exogenous PKL pathway and yeast expressing and exogenous glucoamylase (data not shown).

What is claimed is:

1. Modified yeast cells derived from parental yeast cells, the modified yeast cells comprising:
   (a) a genetic alteration that causes the modified yeast cells to produce a decreased amount of functional Cdc42 effector polypeptides compared to the parental yeast cells, wherein the genetic alteration comprises a disruption of a YHR061c gene, or homolog, thereof, encoding a Gic1 polypeptide and/or disruption of a YDR309c gene, or homolog, thereof, encoding a Gic2 polypeptide, present in the parental yeast cells; and
   (b) an exogenous gene encoding a carbohydrate processing enzyme;
   wherein the modified yeast cells demonstrate increased alcohol production and/or increased lysine production compared to the parental yeast cells under equivalent fermentation conditions.

2. The modified yeast cells of claim 1, wherein the genetic alteration reduces or prevents the production of functional Gic1 and/or Gic2 polypeptides compared to the parental yeast cells.

3. The modified yeast cells of claim 1, wherein the modified yeast cells produce a reduced amount, or do not produce a measurable amount of, Gic1 and/or Gic2 polypeptides.

4. The modified yeast cells of claim 1, wherein the disruption is the result of deletion of all or part of the YHR061c gene, or homolog, thereof, and/or the YDR309c gene, or homolog, thereof, respectively.

5. The modified yeast cells of claim 1, wherein the disruption is the result of deletion of a portion of genomic DNA comprising the YHR061c gene, or homolog, thereof, and/or the YDR309c gene, or homolog, thereof, respectively.

6. The modified yeast cells of claim 1, wherein the disruption is the result of mutagenesis of the YHR061c gene, or homolog, thereof, and/or the YDR309c gene, or homolog, thereof, respectively.

7. The modified yeast cells of claim 1, wherein disruption of the YHR061c gene, or homolog, thereof, and/or the YDR309c gene, or homolog, thereof, respectively, is performed in combination with introducing a gene of interest at a corresponding genetic locus.

8. The modified yeast cells of claim 1, wherein the modified yeast cells further comprise one or more genes of the phosphoketolase pathway.

9. The modified yeast cells of claim 8, wherein the genes of the phosphoketolase pathway are selected from the group consisting of phosphoketolase, phosphotransacetylase and acetylating acetyl dehydrogenase.

10. The modified yeast cells of claim 1, further comprising an alteration in the glycerol pathway and/or the acetyl-CoA pathway.

11. The modified yeast cells of claim 1, further comprising an alternative pathway for making ethanol.

12. The modified yeast cells of claim 1, further overexpressing a sugar transporter-like (STL1) polypeptide.

13. The modified yeast cells of claim 1, further comprising a heterologous gene encoding a protein with NAD+-dependent acetylating acetaldehyde dehydrogenase activity.

* * * * *

SEQUENCE LISTING

```
<160> NUMBER OF SEQ ID NOS: 4

<210> SEQ ID NO 1
<211> LENGTH: 314
<212> TYPE: PRT
<213> ORGANISM: Saccharomyces cerevisiae
<220> FEATURE:
<221> NAME/KEY: MISC_FEATURE
<223> OTHER INFORMATION: Gic1; Genbank Accession No. NP_011928

<400> SEQUENCE: 1

Met Thr Glu Gly Lys Arg Leu Gln Gln Met Glu Leu Pro Gln Met Lys
1               5                   10                  15

Ser Ile Trp Ile Asp Glu Asp Gln Glu Met Glu Lys Leu Tyr Gly Phe
            20                  25                  30

Gln Val Arg Gln Arg Phe Met Asn Gly Pro Ser Thr Asp Ser Asp Glu
        35                  40                  45

Asp Ala Asp Glu Asp Leu Gly Ile Val Leu Val Asp Ser Lys Lys Leu
    50                  55                  60
```

```
Ala Leu Pro Asn Lys Asn Asn Ile Lys Leu Pro Leu Pro Asn Tyr
 65                  70                  75                  80

Met Thr Ile Asn Pro Asn Ile Asn Ser Asn His Lys Ser Leu Thr Asn
                 85                  90                  95

Lys Lys Lys Asn Phe Leu Gly Met Phe Lys Lys Asp Leu Leu Ser
            100                 105                 110

Arg Arg His Gly Ser Ala Lys Thr Ala Lys Gln Ser Ser Ile Ser Thr
            115                 120                 125

Pro Phe Asp Phe His His Ile Ser His Ala Asn Gly Lys Arg Glu Asp
            130                 135                 140

Asn Pro Leu Glu Ser His Glu Glu Lys His Asp Val Glu Ser Leu Val
145                 150                 155                 160

Lys Phe Thr Ser Leu Ala Pro Gln Pro Arg Pro Asp Ser Asn Val Ser
                165                 170                 175

Ser Lys Tyr Ser Asn Val Val Met Asn Asp Ser Ser Arg Ile Val Ser
            180                 185                 190

Ser Ser Thr Ile Ala Thr Thr Met Asp Ser His His Asp Gly Asn Glu
            195                 200                 205

Thr Asn Asn Thr Pro Asn Gly Asn Lys Gln Leu Asp Ser Pro Thr Asp
210                 215                 220

Leu Glu Met Thr Leu Glu Asp Leu Arg Asn Tyr Thr Phe Pro Ser Val
225                 230                 235                 240

Leu Gly Asp Ser Val Ser Glu Lys Thr Asn Pro Ser Pro Ser Val
                245                 250                 255

Ser Ser Phe Ser Gly Lys Phe Lys Pro Arg Glu Leu Ser Ala Leu His
            260                 265                 270

Thr Pro Glu Leu Gly Asn Cys Phe Asn Val Asp Gln Ser Leu Asn Ser
            275                 280                 285

Pro Gly Asn Arg Ile Ser Val Asp Asp Val Leu Lys Phe Tyr Tyr Gln
            290                 295                 300

Cys Ser Glu Thr Ser Thr Pro Arg Asn Thr
305                 310

<210> SEQ ID NO 2
<211> LENGTH: 383
<212> TYPE: PRT
<213> ORGANISM: Saccharomyces cerevisiae
<220> FEATURE:
<221> NAME/KEY: MISC_FEATURE
<223> OTHER INFORMATION: Gic2; Genbank Accession No. NP_010595

<400> SEQUENCE: 2

Met Thr Ser Ala Ser Ile Thr Asn Thr Gly Asn Glu Thr Met Asn Leu
  1               5                  10                  15

Pro Gln Met Arg Ser Ile Trp Leu Asp Glu Asp Glu Ala Glu Lys
                 20                  25                  30

Leu Tyr Gly Leu Gln Ala Gln Gln Phe Met Gly Ser Asp Asp Glu Glu
             35                  40                  45

Asn Leu Gly Ile Thr Phe Ile Asn Ser Asp Lys Pro Val Leu Ser Asn
 50                  55                  60

Lys Lys Asn Ile Glu Leu Pro Pro Leu Ser Pro Asn Ser His Pro Ser
 65                  70                  75                  80

Cys His His Arg Arg Ser Asn Ser Asn Ser Ala Lys Ser Lys Glu Ser
                 85                  90                  95

Ser Ser Ser Ser Ser Ser Ala Asn Lys Thr Asn His Lys Lys Val Phe
            100                 105                 110
```

Leu Lys Leu Asn Leu Leu Lys Lys Leu Leu Gly Ala Gln Pro Asp
            115                 120                 125

Ile Arg Gly Lys Gly Ile Ser Thr Pro Phe Asp Phe Gln His Ile Ser
        130                 135                 140

His Ala Asp Thr Arg Asn Gly Phe Gln Asp Glu Gln Leu Gln Glu Pro
145                 150                 155                 160

Ser Ser Leu Ser Thr Glu Ile Lys Asp Asp Tyr Thr Ser Ser Ser Ser
                165                 170                 175

Lys Arg Asp Ser Lys Ser Leu Asn Lys Ala Phe Val Thr Glu Arg Ile
            180                 185                 190

Pro Ala Asn Arg Glu Ser Lys Leu Ile Ser Arg Ser His Glu Asn Lys
        195                 200                 205

Thr Ser Arg Leu Ser Val Ala Arg Ser Ile Ser Val Thr Ser Ser Asn
    210                 215                 220

Tyr Ser Lys Asn Thr Gln Gly Asn Asn His Ser Ile Asn Gly Arg Val
225                 230                 235                 240

Val Ser Thr Ser Thr Met Ala Thr Ser Ile Phe Glu Tyr Ser Pro Asn
                245                 250                 255

Ala Ser Pro Lys Gln Phe Lys Asn Lys Ser His Ala Leu Gly His Arg
            260                 265                 270

Tyr Thr Asn Ser Thr Asp Ser Ser Glu Ser Ser Leu Asp Phe Leu Lys
        275                 280                 285

Asn Tyr Asn Phe Pro Thr Leu Leu Glu Asp Lys Pro Ile Leu Asp Phe
290                 295                 300

Leu Pro Arg Ser Gln Arg Ser Ser Ala Tyr Arg Ser Leu Leu Glu Thr
305                 310                 315                 320

Pro Asn Ser Asn Lys Asp Ser Ala Lys Ala Phe Phe Pro Ser Arg Gln
                325                 330                 335

Ser Pro Leu Pro Lys Arg Arg Asn Ser Ile Ala Thr Pro Ser Pro Gln
            340                 345                 350

Ser Lys Phe Ser Tyr Ser Asp Ser Pro Val Asn His Arg Lys Ser Phe
        355                 360                 365

Asp Asp Val Leu Tyr Ser Phe Asn Gln Leu Glu Pro Leu Gln Thr
    370                 375                 380

<210> SEQ ID NO 3
<211> LENGTH: 1152
<212> TYPE: DNA
<213> ORGANISM: Saccharomyces cerevisiae
<220> FEATURE:
<221> NAME/KEY: misc_feature
<223> OTHER INFORMATION: GIC2/YDR309C; SGDID:S000002717;
      chrIV:1079048..1080199

<400> SEQUENCE: 3

```
atgactagtg caagtattac caatactgga aacgaaacca tgaaccttcc acagatgcgg      60
tcgatttggc tggatgaaga tgaagaagct gaaaaactct acggtctgca ggcccagcaa     120
ttcatgggat ctgatgatga agaaaaccta ggcattactt tcatcaacag cgataaacct     180
gtgctgagta acaagaaaaa cattgagttg cctccacttt caccaaattc acatccgtct     240
tgccaccaca ggagaagtaa ttctaactct gcaaagtcta agaatcatc gtcatcatcg      300 tccagcgcca acaagacaaa tcacaaaaag ttttccttaa gcttaatttt gttgaagaaa     360
aagttgcttg gtgcccaacc ggacataaga ggtaaaggta tctccacacc atttgatttt     420
caacatattt cacatgctga cactagaaat ggattccaag atgagcaatt gcaggaacct     480
```

```
tcatcgctgt ccacagagat taaggacgac tatacctcct cctcaagcaa gcgggattcg      540
aaatcactaa ataaagcttt tgtcactgaa aggatccctg ctaatcgtga aagcaaactc      600
atttcaagat cgcacgaaaa taagacatca agactatcag tcgcgcgttc gatctcagta      660
acgtcctcca attactctaa aaacacacaa ggaaacaatc attccattaa tgggagagtc      720
gtatctacgt caactatggc tacatctatt tttgagtatt ccccaaacgc atctccaaaa      780
caatttaaaa ataagtcaca cgctctgggt catagataca ctaattccac ggattctagt      840
gagtcttcgc tggatttttt gaagaactac aacttcccca cactacttga agataagcct      900
attttagact tcttgcctcg ttctcagagg tcaagcgctt atcgtagcct tttagagacc      960
ccaaactcaa ataaggactc agcaaaagcc ttctttcctt cacgccaaag ccctcttccc     1020
aagagaagaa actctatagc tacgccttct ccacaatcta aattttccta ctctgactcc     1080
cctgtaaacc atagaaaatc tttcgatgat gttctttatt ctttcaacca gctcgagccc     1140
ctgcaaactt aa                                                         1152

<210> SEQ ID NO 4
<211> LENGTH: 945
<212> TYPE: DNA
<213> ORGANISM: Saccharomyces cerevisiae
<220> FEATURE:
<221> NAME/KEY: misc_feature
<223> OTHER INFORMATION: GIC1/YHR061C; SGDID:S000001103;
      chrVIII:221534..222478

<400> SEQUENCE: 4
atgactgaag gaaagaggct gcaacagatg gagcttcctc aaatgaaatc catttggatt       60
gacgaggatc aggaaatgga aaaattgtat ggattccaag taaggcaacg attcatgaat      120
ggacctagta cggattccga tgaagacgcc gacgaagatt taggaattgt tctcgttgac      180
agtaaaaagc tggctttgcc gaacaagaac aacatcaaat tgccccttt gcccaattac       240 atgacgatca accctaacat aaattccaat cacaagtcat taactaataa aaagaagaat      300
ttcctgggca tgttcaaaaa aaaggacctg ttgtcgagga acatgggtc tgccaaaacc       360 gcaaaacagt caagtatatc tacaccattt gattttcacc atatttcgca tgctaatggt      420
aaaagggaag acaaccctct tgagtcgcac gaagaaaaac atgatgtaga atcattagtc      480
aaattcacgt ctttggcacc gcaaccccga ccagattcaa acgtctcttc taaatattcc      540
aatgttgtga tgaacgattc gagcagaata gtgtcttcct ccacaatagc tacaacgatg      600
gattctcacc acgatggtaa cgaaaccaac aataccccaa atggcaataa gcaattagac      660
tcgcctacag atttggaaat gaccttggaa gacttgagaa attatacatt tccttctgtt      720
cttggagata gcgtcagcga aaagaccaat ccttcctctc cctctgtttc atcattttct      780
ggcaaattca agccaagaga gttgagtgcg ctacatacgc ccgaattagg aaattgtttc      840
aatgtagatc agtcgctaaa ttcccctggt aacagaatat ctgtggatga cgtgctaaaa      900
ttctactatc aatgtagtga aactagtact cctcgaaata cctga                     945
```